(12) United States Patent
Cafiero et al.

(10) Patent No.: US 9,427,376 B2
(45) Date of Patent: Aug. 30, 2016

(54) PROCESS FOR PREPARING PHARMACEUTICAL FORMULATIONS FOR INHALATION COMPRISING A HIGH-DOSAGE STRENGTH ACTIVE INGREDIENT

(71) Applicant: CHIESI FARMACEUTICI S.p.A., Parma (IT)

(72) Inventors: Claudio Cafiero, Parma (IT); Federico Tosini, Parma (IT)

(73) Assignee: CHIESI FARMACEUTICI S.p.A., Pama (IT)

( * ) Notice: Subject to any disclaimer, the term of this patent is extended or adjusted under 35 U.S.C. 154(b) by 54 days.

(21) Appl. No.: 14/483,478

(22) Filed: Sep. 11, 2014

(65) Prior Publication Data

US 2015/0104516 A1 Apr. 16, 2015

(30) Foreign Application Priority Data

Oct. 10, 2013 (EP) ..................................... 13188042

(51) Int. Cl.
| | |
|---|---|
| *A61J 3/02* | (2006.01) |
| *A61K 9/14* | (2006.01) |
| *B02C 17/02* | (2006.01) |
| *B01F 3/20* | (2006.01) |
| *B01F 9/00* | (2006.01) |
| *B01F 15/02* | (2006.01) |
| *B01F 3/18* | (2006.01) |

(52) U.S. Cl.
CPC .................. *A61J 3/02* (2013.01); *A61K 9/145* (2013.01); *B01F 3/18* (2013.01); *B01F 3/2071* (2013.01); *B01F 9/00* (2013.01); *B01F 15/0224* (2013.01); *B02C 17/02* (2013.01)

(58) Field of Classification Search
None
See application file for complete search history.

(56) References Cited

FOREIGN PATENT DOCUMENTS

| EP | 2457645 | 5/2012 |
|---|---|---|
| WO | 95/11666 | 5/1995 |
| WO | WO9511666 | * 5/1995 |

OTHER PUBLICATIONS

European Search Report in Application No. 13188042.9 issued Mar. 13, 2014.

* cited by examiner

*Primary Examiner* — Robert A Wax
*Assistant Examiner* — Melissa Mercier
(74) *Attorney, Agent, or Firm* — Oblon, McClelland, Maier & Neustadt, L.L.P

(57) ABSTRACT

Cohesive high-dosage strength micronized active ingredients may be dispersed in dry powder formulations for inhalation comprising carrier particles, by use of the apparatus described herein.

20 Claims, 1 Drawing Sheet

PROCESS FOR PREPARING PHARMACEUTICAL FORMULATIONS FOR INHALATION COMPRISING A HIGH-DOSAGE STRENGTH ACTIVE INGREDIENT

CROSS REFERENCES TO RELATED APPLICATIONS

This application claims priority to the European Patent Application No. 13188042.9, filed on Oct. 10, 2013, which is incorporated herein by reference in its entirety.

BACKGROUND OF THE INVENTION

1. Field of the Invention

The present invention relates to processes for dispersing a cohesive high-dosage strength micronized active ingredient in a dry powder formulation for inhalation comprising carrier particles, and an apparatus thereof.

2. Discussion of the Background

The administration of pharmacologically active ingredients by inhalation to the airways is a widely used technique especially for the treatment of reversible airway obstruction, inflammation, and hyper-responsiveness.

Some of the most widely used systems for the administration of drugs to the airways are represented by dry powder inhalers (DPIs) which, in turn, can be divided into two basic types: i) single dose inhalers, for the administration of single subdivided doses of the active compound, each single dose being usually filled in a capsule; and ii) multidose inhalers pre-loaded with quantities of active ingredients sufficient for longer treatment cycles.

Drugs intended for inhalation as dry powders by means of DPIs should be used in the form of micronized particles. Micronization is generally achieved by conventional milling processes known to the skilled person.

Although micronization of the drug is essential for deposition into the lower respiratory tract during inhalation, it is also known that the finer are the particles, the stronger are the cohesion forces among them. Strong cohesion forces hinder the handling of the powder during the manufacturing process (pouring, filling). Moreover they reduce the flowability of the particles, while favoring, inside the multidose DPI's, the agglomeration and the adhesion thereof to the walls of the reservoir. Said phenomena impair the loading of the powder from the reservoir to the metering chamber and, hence, give rise to handling and metering accuracy problems.

Poor flowability is also detrimental to the respirable fraction of the delivered dose in that the active particles are unable to properly leave the inhaler, essentially because they remain adhered to the interior of the inhaler and/or leave the inhaler as large agglomerates; agglomerated particles, in turn, cannot reach the bronchiolar and alveolar sites of the lungs. The uncertainty as to the extent of agglomeration of the particles between each actuation of the inhaler and, also, among inhalers and different batches of particles, leads to poor dose reproducibility as well.

For these reasons, powders for inhalation are commonly formulated by diluting the micronized drug in a pharmacologically inert physiologically acceptable excipient of coarser particles to yield the so-called "interactive ordered mixtures".

However, it has been found that particularly cohesive active ingredients to be delivered at relatively high doses, e.g. equal to or higher than 100 µg per actuation, are difficult to disperse, and form agglomerates even though they are diluted by mixing with coarse excipient particles.

The presence of the agglomerates leads to problems in the manufacturing of inhalable powder formulations with a good uniformity distribution of the active ingredient in the blend as well as a good dosage reproducibility and high respirable fraction upon administration by DPI's.

In view of the problems outlined above, it would be highly advantageous to provide a process for preparing powder formulations for inhalation comprising cohesive active ingredients to be delivered at high doses per actuation capable of achieving a good dispersion of active particles when properly diluted with coarse carrier particles.

The problem is solved by the process of the present invention.

SUMMARY OF THE INVENTION

Accordingly, it is one object of the present invention to provide novel processes for preparing powder formulations for inhalation.

It is another object of the present invention to provide novel processes for preparing powder formulations for inhalation comprising cohesive active ingredients to be delivered at high doses per actuation capable of achieving a good dispersion of active particles when properly diluted with coarse carrier particles.

It is another object of the present invention to provide novel apparatus for carrying out such a process.

These and other objects, which will become apparent during the following detailed description, have been achieved by the inventors' discovery of the processes and apparatus described below.

Thus, according to a first aspect, the present invention provides a process for dispersing a cohesive high-dosage strength micronized active ingredient in dry powder formulations comprising carrier particles, said process comprising the steps of:

(i) providing a dispersion capsule comprising a cylindrical room (1) with a lateral boundary made of a sieving mesh (2), said room containing grinding balls (3), being closed by a screw cap (4) on the top, two longitudinal rods (6), and a disk (5) wherein the capsule is connected to said disk by said two longitudinal rods;

(ii) loading said active ingredient and an aliquot of the carrier particles in the capsule of step (i);

(iii) fitting said capsule to a drum, filled with the remaining part of the carrier;

(iv) inserting the drum into a rotating body mixer apparatus; and (v) operating said rotating body mixer to mix the whole powder.

The present invention also provides an apparatus in form of capsule for dispersing a cohesive high-dosage strength micronized active ingredient, said capsule comprising a cylindrical room (1) with a lateral boundary made of a sieving mesh (2), said room containing grinding balls (3) being closed by a screw cap (4) on the top, two longitudinal rods (6), and a disk (5) wherein the capsule is connected to said disk by said two longitudinal rods.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1:
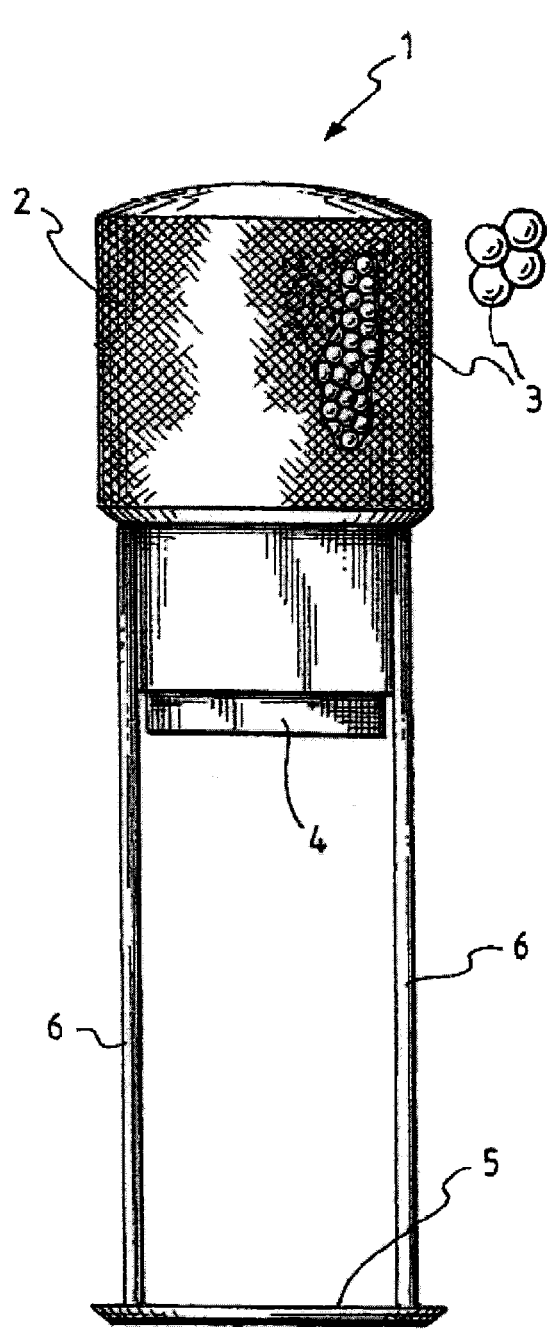
FIG. 1 shows a front elevational view of the dispersion capsule according to the invention.
Figure 2:
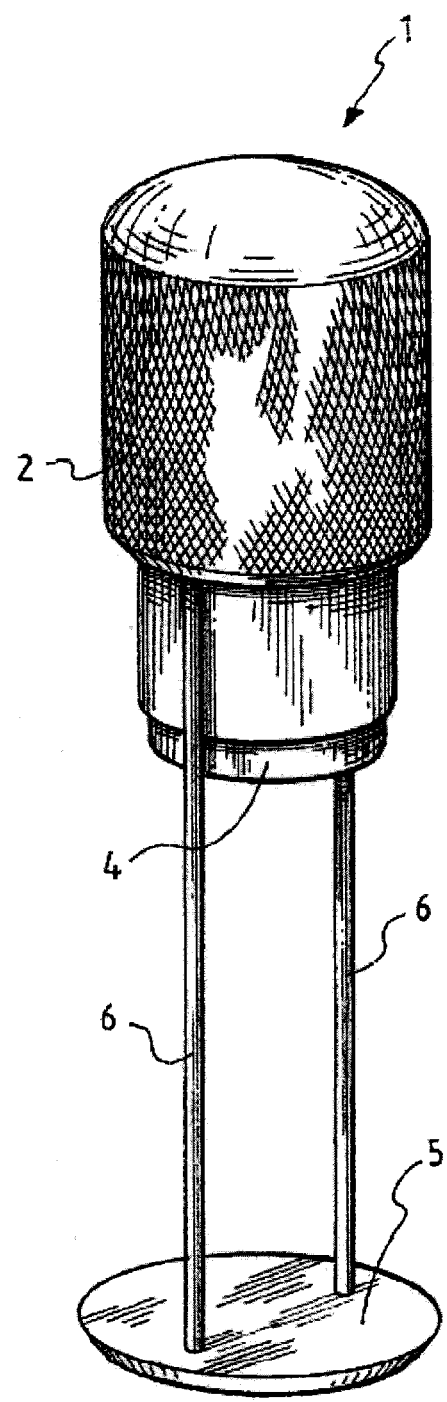
FIG. 2 is a perspective view of the dispersion capsule of FIG. 1.

The term "drum" refers to a tank of variable capacity, made of an inert material, usually of steel, preferably of stainless steel, having a porthole (opening) to be fitted with the screw top (4). The drum is typically used for the transport, process manipulation and storage of the product.

The term "cohesive active ingredient" means a micronized powder having a Specific Energy value equal to or higher than 10 mJ/g. The Specific Energy can be determined by applying the Freeman technology and the FT4 universal powder rheometer that measures bulk, flow and shear properties. During dynamic testing, the rotational and axial forces acting on an helical blade are measured as it passes through a sample. Basic flow energy (BFE) is determined from these data and is regarded as a measure of the rheology or resistance to flow of the powder. The Specific Energy (SE) is a measure of how powder will flow in an unconfined or low stress environment and it is considered as a powder cohesion index. See Zauner, J., et al., Quantitative Study of Process and Material Parameters on Flow Behavior and Powder Binder Separation of Feedstocks: Experimental Design 3D Simulation Model and Balance Model for Separation in Suspensions; In *ADVANCES IN POWDER METALLURGY AND PARTICULATE MATERIALS*, vol. 1-4, PTS 1-13, 2008, 1-13, which is incorporated herein by reference in its entirety. The Surface Energy is calculated from the energy required to establish a particular flow pattern in a conditioned, precise volume of powder as reported in Freeman, R., Measuring the flow properties of consolidated, conditioned and aerated powders—a comparative study using a powder rheometer and a rotational shear cell, *Powder Technology*, 2007, 174, 25-33, which is incorporated herein by reference in its entirety. The flow pattern is an upward clockwise motion of the blade, generating gentle lifting and low stress flow of the powder.

The term "rotating body mixer" refers to an apparatus which creates particle movement by rotation of the entire mixer shell or body.

The term "carrier particles" refers to particles constituted of any pharmacologically-inert (not-therapeutically active) physiologically acceptable material.

For the purpose of the present invention, the term "high-dosage strength active ingredients" are those to be delivered using a dry powder inhaler (DPI) device whose nominal dose delivered after each actuation of the inhaler is equal to or higher than 100 micrograms (μg). The term "actuation" means the release of active ingredients from the device by a single activation (e.g. mechanical or breath).

The term "dispersing" refers to obtaining a good homogeneity of the active ingredient in the powder formulation, wherein no agglomerates of micronized particles of said active ingredient are present as visually determined or as determined by other methods known to the skilled person in the art such as sieving or Near Infrared Spectrophotometry provided with a microscopy imaging system (Near Imaging).

The expression "good homogeneity" refers to a powder wherein, upon mixing, the uniformity of distribution of a component, expressed as coefficient of variation (CV) also known as relative standard deviation (RSD), is less than 5.0%. It is usually determined according to methods known to the skilled person, for instance by taking samples from different parts of the powder and testing the component by HPLC or other equivalent analytical methods.

The term "coarse" means a substance having a size at least of few tens of microns.

In general terms, the particle size of the particles is quantified by measuring a characteristic equivalent sphere diameter, known as volume diameter, by laser diffraction.

The particle size can also be quantified by measuring the mass diameter by means of suitable known instrument such as, for instance, the sieve analyzer.

The volume diameter (VD) is related to the mass diameter (MD) by the density of the particles (assuming a size independent density for the particles).

The particle size of the active ingredients and of the fraction of excipient fine particles is expressed in terms of volume diameter, while that of the coarse particles is expressed in terms of mass diameter.

The particles have a normal (Gaussian) distribution which is defined in terms of the volume or mass median diameter (VMD or MMD) which corresponds to the volume or mass diameter of 50% by weight of the particles, and, optionally, in terms of volume or mass diameter of 10% and 90% of the particles, respectively.

Another common approach to define the particle size distribution is by means of three values: i) the median diameter d(0.5) which is the diameter where 50% of the distribution is above and 50% is below; ii) d(0.9), where 90% of the distribution is below this value; iii) d(0.1), where 10% of the distribution is below this value.

Upon aerosolization, the particle size is expressed as mass aerodynamic diameter (MAD), while the particle size distribution is expressed in terms of mass median aerodynamic diameter (MMAD) and Geometric Standard Deviation (GSD). The MAD indicates the capability of the particles of being transported suspended in an air stream. The MMAD corresponds to the mass aerodynamic diameter of 50% by weight of the particles.

The term "hard pellets" refers to spherical or semispherical units whose core is made of coarse excipient particles.

The term "spheronization" refers to the process of rounding off of the particles which occurs during the treatment.

The term "good flowability" refers to a formulation that is easy handled during the manufacturing process and is able to ensure an accurate and reproducible delivering of the therapeutically effective dose.

Flow characteristics can be evaluated by different tests such as angle of repose, Carr's index, Hausner ratio or flow rate through an orifice.

The flow properties were tested by measuring the flow rate through an orifice according to the method described in the European Pharmacopeia (Eur. Ph.) 7.3, $7^{th}$ Edition, which is incorporated herein by reference in its entirety.

The expression "respirable fraction" refers to an index of the percentage of active particles which would reach the lungs in a patient.

The respirable fraction is evaluated using a suitable in vitro apparatus such as Andersen Cascade Impactor (ACI), Multi Stage Liquid Impinger (MLSI), Next Generation Impactor (NGI) or other apparatus known to the skilled person, according to procedures reported in common Pharmacopoeias, in particular in the European Pharmacopeia (Eur. Ph.) 7.3, $7^{th}$ Edition, which is incorporated herein by reference in its entirety. It is calculated by the percentage ratio of the fine particle mass (formerly fine particle dose) to the delivered dose.

The delivered dose is calculated from the cumulative deposition in the apparatus, while the fine particle mass is calculated from the deposition of particles having a diameter <5.0 microns or by other methods known to the skilled person in the art.

The present invention provides a process for the preparation of a powder formulation for inhalation comprising carrier particles, said process providing a good dispersion of cohesive, high-dosage strength micronized active ingredients in the powder formulation, and hence a good homogeneity.

The process of the present invention turned out to be faster and more reproducible than processes based on other systems of mixing.

In the powder formulation obtained by the process of the present invention, agglomerates of the active ingredient are not present, giving rise to an improved uniformity of distribution of the active ingredient, and hence of the reproducibility of the delivered dose.

No loss of active ingredient was observed either.

Furthermore, powder formulations obtained by the process of the present invention turned to be more flowable than those processed based on the different systems of mixing as a lesser amount of fine carrier particles are produced during the dispersion step.

The carrier particles may comprise any pharmacologically-inert, physiologically acceptable substance, amorphous or crystalline, or combination thereof; preferred materials are crystalline sugars and for example monosaccharides such as glucose or arabinose, or disaccharides such as maltose, sucrose, dextrose and lactose. Polyalcohols such as mannitol, sorbitol, maltitol, and lactitol may also be used.

The preferred material is lactose, more preferably α-lactose monohydrate. Examples of commercial α-lactose monohydrate are Capsulac® and Pharmatose®. An example of commercial mannitol is Pearlitol®.

The carrier particles usually comprise coarse carrier particles.

Said coarse particles shall have a mass median diameter equal to or higher than 80 microns, preferably equal to or greater than 125 microns, more preferably equal to or greater than 150 microns, even more preferably equal to or greater than 175 microns.

Advantageously, all the coarse particles have a mass diameter in the range 50-1000 microns, preferably comprised between 60 and 500 micron.

In certain embodiments of the invention, the mass diameter of said coarse particles might be comprised between 80 and 200 microns, preferably between 90 and 150 microns, while in another embodiment, the mass diameter might be comprised between 200 and 400 microns, preferably between 210 and 355 microns.

Preferably, the mass diameter of the coarse particles is comprised between 210 and 355 microns.

In general, the skilled person shall select the most appropriate size of the coarse excipient particles by sieving, using a proper classifier.

When the mass diameter of the coarse particles is comprised between 200 and 400 microns, the coarse excipient particles preferably have a relatively highly fissured surface, that is, a surface on which there are clefts and valleys and other recessed regions, referred to herein collectively as fissures. The term "relatively highly fissured" coarse particles can be defined in terms of fissure index or rugosity coefficient as described in WO 01/78695 and WO 01/78693, which are incorporated herein by reference in their entireties, and they may be characterized according to the description therein reported. Advantageously, the fissure index of said coarse particles is of at least 1.25, preferably of at least 1.5, more preferably of at least 2.0, while the rugosity coefficient is of at least 1.25.

The carrier may also comprise fine particles of a physiologically acceptable material in admixture with the coarse particles. Typically, said physiologically acceptable materials are those reported above for the coarse carrier particles, and preferably, both the coarse and fine particles are constituted of the same physiologically acceptable active material, more preferably alpha-lactose monohydrate.

Generally, the fine carrier particles have a MMD of less than 35 microns, preferably of less than 15 microns, more preferably from 2 to 10 microns.

The carrier may further comprise one or more additives to promote the release of the active particles from the carrier particles on actuation of the inhaler. The additive may include a given material or a combination of more materials.

Advantageously the additive is a material with antiadherent properties such as the amino acids leucine and isoleucine. The additive may also contain one or more water-soluble surface active materials, for example lecithin, in particular soya lecithin.

Preferably, the additive is a water-insoluble lubricant such as magnesium stearate, sodium stearyl fumarate, sodium lauryl sulphate, stearyl alcohol, stearic acid, and sucrose monopalmitate. More preferably, the additive is magnesium stearate.

In a particular embodiment of the invention, the carrier consists of:

i) a fraction of microparticles having a MMD lower than 15 microns constituted of a mixture of particles of alpha-lactose monohydrate and particles of magnesium stearate (the fine carrier fraction); and ii) a fraction of particles of alpha lactose monohydrate having a diameter higher than 175 microns.

The microparticles (i) may be prepared according to the methods disclosed in WO 01/78693, which is incorporated herein by reference in its entirety.

For example, said microparticles could be prepared by mixing and then micronizing the two components together by milling. Alternatively, each component can be micronized individually and then combined by mixing.

In certain embodiments of the present invention, the microparticles fraction is composed from 90 to 99% by weight of α-lactose monohydrate particles and from 10 to 1% by weight of magnesium stearate particles; in a particularly preferred embodiment, the microparticles fraction is composed by 98% of α-lactose monohydrate particles and by 2% of magnesium stearate particles. The weight ratio between the microparticles fraction and the coarse particles is from 15:85 to 5:95 respectively, even more preferably 10:90.

As a first step, the process of the present invention comprises the use of a dispersion capsule comprising a cylindrical room (1) with a lateral boundary made of a sieving mesh (2), said room containing grinding balls (3) and being closed by a screw cap on the top (4), wherein the dispersion capsule is connected to a disk (5) by two longitudinal rods (6).

The skilled person shall use a cylindrical room and a screw (4) cap of a size capable of passing through the porthole of the dr The dispersion capsule is advantageously connected to the drum by a fastening clamp.

The skilled person shall also adjust the length of the cylindrical room (1) and of the rods (6) depending on the product batch size.

The size of the meshes of the sieving screen shall be suitably selected by the skilled person depending on the size of the coarse carrier particles. Preferably, the mesh size is comprised between 600 μm and 1200 μm (microns).

The disk (5) and the rods (6) can be made of any suitable inert material, advantageously of steel, preferably of stainless steel.

Also the balls inside the dispersion capsule may be made of any suitable inert material such as steel or hard teflon, preferably of stainless steel, more preferably of stainless steel type AISI 316.

Advantageously, the diameter of the balls is less than 5 cm, preferably of 0.5 to 5 cm, more preferably 1 to 5 cm, even more preferable about 2 cm.

In a second step, one or more micronized active ingredients and an aliquot of the carrier particles are loaded in the dispersion capsule.

The ratio between the micronized active ingredient particles and said part of the carrier particles might advantageously be comprised between 1:0.5 and 1:10 by weight, preferably between 1:2 and 1:5 by weight.

In a third step, the dispersion capsule of the present invention is fitted to a drum filled with the remaining part of the carrier and fixed with a clamp.

Depending on the size of the batch, the skilled person shall select a drum of the proper capacity.

The drum is then inserted into a mixer apparatus.

Any rotating body mixer apparatus commercially available can be suitably used. Said mixers include V-shaped and double cone apparatus.

Mixers of this type such as Turbula™ or DynaMIX™ are commercially available from Bachofen AG (Muttenz, Switzerland).

Afterwards, all the powder is mixed for a time not longer than 40 minutes, advantageously not longer than 30 minutes, preferably from 5 to 20 minutes, in such a way as that the portion comprising the active ingredient(s) is forced through the meshes of the sieve screening.

In a general way, the skilled person shall suitably adjust the speed of rotation of the mixer depending on the size of the processed batch.

At the end of the process, the resulting powder can be harvested and used as such.

Otherwise, optionally, the powder can be poured into a sieving machine available from Frewitt (Fribourg, Switzerland).

The skilled person shall select the proper mesh size of the sieving screen depending on the particle size of the coarse carrier particles.

The powder collected from the Frewitt machine can be subjected to a further mixing step in suitable known apparatus, such as a Turbula™ mixer or DynaMIX™ mixer. In a general way, the skilled person shall adjust the time of mixing and the speed of rotation of the mixer depending on the desired degree of homogeneity.

When the particle size of the coarse carrier particles is comprised between 150 and 400 microns, preferably between 212 and 355 microns, the powder formulation are preferably in the form of "hard pellets". This can be obtained by subjecting the powder mixture to a spheronization step that shall be carried out for at least two hours, even more preferably for four hours.

The active ingredient particles referred to throughout the specification will comprise an effective amount of at least one high-dosage strength active substance that can be delivered to the lungs in the form of a powder for inhalation by means of a DPI. Advantageously, the high-dosage strength active agents are those active ingredients whose nominal dose is equal to or higher than 100 μg (microg), more advantageously equal to or higher than 200 μg, preferably equal to or higher than 400 μg.

In some embodiments of the invention, nominal dose might be of 600 μg, or 800 μg, or 1200 μg.

The weight ratio of the active agent to the carrier in the formulation (as opposed to the weight ratio of the active agent to the carrier loaded into the capsule) is advantageously from 0.005:1 to 0.15:1. In some embodiments, it might be from 0.01:1 to 0.1:1. In other embodiments, it might be from 0.02:1 to 0.12:1.

Suitable therapeutically active agents include drugs which are usually administered by inhalation for the prevention and/or treatment of respiratory diseases. Examples of said respiratory drugs are the phosphodiesterase inhibitors disclosed in WO 2008/006509, WO 2009/077068, WO 2009/127320, WO 2009/018909, and WO 2010/089107, all of which are incorporated herein by reference in their entireties, or the anti-muscarinic agents disclosed in WO 2011/161018, WO 2011/160918, WO 2011/160919, WO 2010/015324, and WO 2010/072338, all of which are incorporated herein by reference in their entireties. In certain embodiments of the present invention, the aforementioned active agents can be used in combination with additional active ingredients selected from the group of corticosteroids and/or beta$_2$-agonists, provided that they are compatible with one another under conditions of storage and use.

Typically, at least 90% of the particles of each micronized active ingredient have a diameter equal to or lower than 6 microns. Advantageously at least 90% of all said micronized particles of the active ingredients have a volume diameter lower than 6.0 microns, preferably equal to or lower than 5.0 microns, and the volume median diameter of said particles is from 1.2 to 2.5 microns, preferably from 1.3 to 2.2 microns.

Advantageously, the process of the invention is applied to micronized active ingredients having a cohesivity expressed as Specific Energy value equal to or higher than 10 mJ/g, preferably higher than 15 mJ/g, more preferably higher than 20 mL/g. The Specific Energy shall be determined according to reported in the 'Definitions' paragraph.

Other features of the invention will become apparent in the course of the following descriptions of exemplary embodiments which are given for illustration of the invention and are not intended to be limiting thereof.

EXAMPLES

Example 1

Preparation of a Powder Formulation Comprising an Anti-Muscarinic Agent as Active Ingredient The composition of the powder formulation is reported in Table 1.

TABLE 1

C1 dry powder formulation.

| Components | Amounts | | Single dose |
|---|---|---|---|
| | Per shot of the inhaler | | |
| | mg | % | μg |
| Compound C1 | 0.2 | 2.0 | 200 |
| Alpha-lactose monohydrate 212-355 μm | 8.82 | 88.2 | |
| Microparticles | 0.98 | 9.8 | |
| Total weight | 10 | | |

A 4 kg batch size of the dry powder formulation was prepared as described as follows. The anti-muscarinic compound (R)-3-[bis-(3-fluoro-phenyl)-methoxycarbonyloxy]-1-(2-oxo-2-thiophen-2-yl-ethyl)-1-azonia-bicyclo[2.2.2]octane chloride, referred to as C1 in WO 2010/015324, which is incorporated herein by reference in its entirety, was subjected to micronization according to standard milling techniques.

Particles of α-lactose monohydrate having a mean particle size of less than 250 microns, and magnesium stearate particles having a mean particle size of less than 35 microns in a ratio 98:2 percent by weight were co-micronized by milling in a jet mill operating under nitrogen to obtain the fraction of co-micronized particles indicated as microparticles.

Said microparticles were mixed in a Turbula mixer for 4 hours with fissured coarse particles of α-lactose monohydrate having a mass diameter comprised between 212-355 microns in the ratio 90:10 percent by weight, to obtain the Carrier.

The micronized compound C1 and an aliquot of the Carrier in a 1:1 ratio by weight with C1 were loaded in the dispersion capsule fitted with sieving mesh (2) of size of 1 mm. The whole apparatus is made of stainless steel. The grinding balls are made of stainless steel as well and have a diameter of 2 cm.

The dispersion capsule was fitted to a 22 l stainless steel drum, filled with an aliquot of remaining part of the Carrier.

The drum was inserted into a DynaMIX™ mixer apparatus which was operated for 20 minutes.

The collected powder does not show any agglomerate upon visual inspection. It was characterized in terms of the uniformity of distribution of the active ingredients and aerosol performances after loading it in the multidose dry powder inhaler described in WO 2004/012801, which is incorporated herein by reference in its entirety.

The uniformity of distribution of the active ingredients was evaluated by withdrawing 20 samples from different parts of the powder and determined by HPLC. Each sample has a mass unit comprised between 1 and 3 doses of the active ingredient. The results (mean value±RSD) are reported in Table 2.

The evaluation of the aerosol performance was carried out using the New Generation Impactor (NGI) according to the conditions reported in the European Pharmacopeia $6^{th}$ Ed 2008, par 2.9.18, which is incorporated herein by reference in its entirety.

After aerosolization of 3 doses from the inhaler device, the ACI apparatus was disassembled and the amounts of drug deposited in the stages were recovered by washing with a solvent mixture and then quantified by High-Performance Liquid Chromatography (HPLC). The following parameters, were calculated: i) the delivered dose which is the amount of drug delivered from the device recovered in the all parts of impactor; ii) the fine particle mass (FPM) which is the amount of delivered dose having a particle size equal to or lower than 5.0 microns; iii) the fine particle fraction (FPF) which is the percentage of the fine particle dose; iv) the MMAD. The results (mean±RSD) are reported in Table 2.

TABLE 2

| | |
|---|---|
| Uniformity of distribution | 98.2 (±1.1) |
| Delivered Dose (μg) | 160.4 |
| Fine Particle Mass <5 μm (μg) | 81.5 |
| Fine Particle Fraction <5 μm (%) | 50.8 |

As it can be appreciated, the powder formulation processed according to the process of the present invention shows a good uniformity of distribution of the active ingredient as demonstrated by the low RSD as well as good aerosol performances.

Example 2

Preparation of a Powder Formulation Comprising a Phosphodiesterase Inhibitor as Active Ingredient The composition of the powder formulation is reported in Table 3.

TABLE 3

C2 dry powder formulation.

| Components | Amounts | | Single dose |
|---|---|---|---|
| | Per shot of the inhaler | | |
| | mg | % | μg |
| Compound C2 | 0.4 | 4.0 | 400 |
| Alpha-lactose monohydrate 212-355 μm | 9.0 | 90.0 | |
| Microparticles | 0.96 | 9.6 | |
| Total weight | 10 | | |

A batch size of the dry powder formulation is prepared as described as follows. The phosphodiesterase inhibitor (−)-3-cyclopropylmethoxy-4-methanesulfonylamino-benzoic acid 1-(3-cyclopropylmethoxy-4-difluoromethoxy-phenyl)-2-(3,5-dichloro-1-oxy-pyridin-4-yl)-ethyl ester referred to as C2 in WO 2010/089107, which is incorporated herein by reference in its entirety, is micronized by methods known in the art, to prepare the active substance in the form of particles having a typical particle size suitable for inhalation.

The Carrier is prepared as reported in the Example 1.

The micronized active ingredient and the Carrier are processed as reported in Example 1.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A process for dispersing a cohesive, high-dosage strength micronized active ingredient in a dry powder formulation comprising carrier particles, said process comprising:

(i) loading said active ingredient and a portion of said carrier particles in a dispersion capsule comprising a cylindrical room (1) with a lateral boundary made of a sieving mesh (2), said room (1) containing grinding balls (3), which can be closed by a screw cap (4) on the top, two longitudinal roads (6), and a disk (5), wherein the capsule is connected to said disk by said two longitudinal rods;

(ii) fitting said capsule to a drum, filled with the remaining part of the carrier;

(iii) inserting said drum into a rotating body mixer apparatus; and (iv) operating said rotating body mixer to mix the whole powder.

2. A process according to claim 1, wherein said active ingredient is contained in said dry powder formulation in an amount sufficient to deliver a nominal dose equal to or higher than 100 μg per actuation of an inhaler.

3. A process according to claim 2, wherein said nominal dose is equal to or higher than 200 μg.

4. A process according to claim 3, wherein said nominal dose is equal to or higher than 400 μg.

5. A process according to claim 1, wherein said active ingredient is a drug which is usually administered by inhalation for the prevention and/or treatment of respiratory diseases.

6. A process according to claim 5, wherein said drug is a phosphodiesterase inhibitor or an anti-muscarinic agent.

7. A process according to claim 1, wherein said carrier comprises a pharmacologically-inert, physiologically acceptable substance.

8. A process according to claim 7, wherein said substance is one or more crystalline sugars selected from the group consisting of glucose, arabinose, maltose, sucrose, a dextrose, and lactose.

9. A process according to claim 8, wherein said sugar is alpha-lactose monohydrate.

10. A process according to claim 7, wherein said carrier particles have a mass median diameter equal to or higher than 80 microns.

11. A process according to claim 10, wherein said mass median diameter is equal to or greater than 175 microns.

12. A process according to claim 7, wherein said carrier further comprises one or more additives.

13. A process according to claim 1, wherein said active ingredient and said carrier are loaded into said dispersion capsule in a weight ratio of 1:0.5 and 1:10.

14. A process according to claim 1, wherein said active ingredient and said carrier are loaded into said dispersion capsule in a weight ratio of 1:2 and 1:5.

15. A process according to claim 1, wherein the weight ratio of said active agent to said carrier particles is from 0.005:1 to 0.15:1.

16. A process according to claim 1, wherein the weight ratio of said active agent to said carrier particles is from 0.01:1 to 0.1:1.

17. A process according to claim 1, wherein the weight ratio of said active agent to said carrier particles is from 0.02:1 to 0.12:1.

18. An apparatus in the form of a capsule for dispersing a cohesive high-dosage strength micronized active ingredient, said capsule comprising a cylindrical room (1) with a lateral boundary made of a sieving mesh (2) containing grinding balls (3) and which can be closed by a screw cap (4) on the top, two longitudinal rods (6), and a disk (5) wherein the capsule is connected to said disk by said two longitudinal rods.

19. An apparatus according to claim 18, wherein said sieving mesh has a size comprised between 600 μm and 1200 μm.

20. An apparatus according to claim 18, wherein said grinding balls (3), said disk (5) and said rods (6) are made of stainless steel.

* * * * *